(12) United States Patent
Wöhrle et al.

(10) Patent No.: US 7,780,447 B2
(45) Date of Patent: Aug. 24, 2010

(54) DENTAL IMPLANT SYSTEM

(75) Inventors: Peter S. Wöhrle, Corona Del Mar, CA (US); Duaine E. Griffith, Mission Viejo, CA (US)

(73) Assignee: Nobel Biocare Services AG, Glattbrugg (CH)

( * ) Notice: Subject to any disclaimer, the term of this patent is extended or adjusted under 35 U.S.C. 154(b) by 230 days.

(21) Appl. No.: 11/406,626

(22) Filed: Apr. 19, 2006

(65) Prior Publication Data

US 2006/0188846 A1    Aug. 24, 2006

Related U.S. Application Data

(62) Division of application No. 10/341,531, filed on Jan. 13, 2003, now abandoned.

(60) Provisional application No. 60/347,723, filed on Jan. 11, 2002.

(51) Int. Cl.
    *A61C 8/00* (2006.01)
(52) U.S. Cl. .................................................. 433/174
(58) Field of Classification Search .......... 433/172–176
    See application file for complete search history.

(56) References Cited

U.S. PATENT DOCUMENTS

| 2,112,007 | A | 3/1938 | Adams |
| 3,849,887 | A | 11/1974 | Brainin |
| 4,051,598 | A | 10/1977 | Sneer |
| 4,416,629 | A | 11/1983 | Mozxary et al. |
| 4,468,200 | A | 8/1984 | Münch |
| 4,624,673 | A | 11/1986 | Meyer |
| 4,713,003 | A | 12/1987 | Symington et al. |

(Continued)

FOREIGN PATENT DOCUMENTS

| CH | 413224 | 5/1966 |

(Continued)

OTHER PUBLICATIONS

Strub et al., "The Re Implant® System for Immediate Implant Placement". Journal of Esthetic Dentistry 1997, vol. 9, pp. 187-196.

(Continued)

*Primary Examiner*—Cris L Rodriguez
*Assistant Examiner*—Matthew M Nelson
(74) *Attorney, Agent, or Firm*—Knobbe, Martens, Olson & Bear LLP

(57) ABSTRACT

A dental implant assembly for supporting a dental prosthesis. The assembly comprises a dental implant and an abutment. The dental implant comprises a body portion, a collar portion and a central bore. The body portion is located at a distal end of the dental implant and is configured to lie at least substantially below a crest of a patient's jawbone. The collar portion is located at a proximal end of the dental implant and forms an abutment mating surface which defines an outer edge that has a generally scalloped shape. The central bore extends through the collar portion and into the implant body portion. The central bore includes a threaded portion and a post portion. The abutment comprises a post configured to fit within the post portion of the central bore and an implant mating surface that is configured to mate with the abutment mating surface of the dental implant.

10 Claims, 7 Drawing Sheets

U.S. PATENT DOCUMENTS

| | | | |
|---|---|---|---|
| 4,812,120 A | | 3/1989 | Flanagan et al. |
| 4,856,994 A | * | 8/1989 | Lazzara et al. ............... 433/173 |
| 4,960,381 A | | 10/1990 | Niznick |
| 5,004,422 A | | 4/1991 | Propper |
| 5,035,619 A | | 7/1991 | Daftary |
| 5,049,074 A | | 9/1991 | Otani et al. |
| 5,125,839 A | | 6/1992 | Ingber et al. |
| 5,246,370 A | | 9/1993 | Coatoam |
| 5,282,746 A | | 2/1994 | Sellers et al. |
| 5,282,747 A | | 2/1994 | Nordin |
| 5,310,343 A | | 5/1994 | Hasegawa et al. |
| 5,316,477 A | | 5/1994 | Calderon |
| 5,328,371 A | | 7/1994 | Hund et al. |
| 5,417,568 A | | 5/1995 | Giglio |
| 5,417,569 A | | 5/1995 | Perisse |
| 5,431,567 A | | 7/1995 | Daftary |
| 5,458,488 A | | 10/1995 | Chalifoux |
| 5,464,440 A | | 11/1995 | Joahansson |
| 5,527,182 A | | 6/1996 | Willoughby |
| 5,584,693 A | | 12/1996 | Nishihara |
| 5,588,838 A | | 12/1996 | Hansson et al. |
| 5,622,500 A | * | 4/1997 | Niznick ...................... 433/173 |
| 5,636,989 A | | 6/1997 | Somborac et al. |
| 5,667,384 A | | 9/1997 | Sutter et al. |
| 5,674,069 A | | 10/1997 | Osorio |
| 5,695,334 A | | 12/1997 | Blacklock et al. |
| 5,759,034 A | | 6/1998 | Daftary |
| 5,779,480 A | | 7/1998 | Groll et al. |
| 5,876,454 A | | 3/1999 | Nanci et al. |
| 5,908,298 A | | 6/1999 | Dürr et al. |
| 5,931,675 A | | 8/1999 | Callan |
| 5,989,027 A | | 11/1999 | Wagner et al. |
| 5,989,029 A | | 11/1999 | Osorio et al. |
| 6,012,923 A | | 1/2000 | Bassett et al. |
| 6,024,567 A | | 2/2000 | Callan |
| 6,142,782 A | * | 11/2000 | Lazarof ...................... 433/174 |
| 6,162,054 A | | 12/2000 | Takacs |
| 6,164,969 A | | 12/2000 | Dinkelacker |
| 6,174,167 B1 | | 1/2001 | Wöhrle |
| 6,217,331 B1 | | 4/2001 | Rogers et al. |
| 6,217,333 B1 | | 4/2001 | Ercoli |
| 6,227,858 B1 | | 5/2001 | Lundgren |
| 6,231,342 B1 | | 5/2001 | Osorio et al. |
| 6,273,720 B1 | * | 8/2001 | Spalten ...................... 433/173 |
| 6,280,195 B1 | | 8/2001 | Broberg et al. |
| 6,283,753 B1 | | 9/2001 | Willoughby |
| 6,283,754 B1 | | 9/2001 | Wöhrle |
| 6,287,115 B1 | | 9/2001 | Lustig et al. |
| 6,312,260 B1 | | 11/2001 | Kumar et al. |
| 6,350,126 B1 | | 2/2002 | Levisman |
| 6,364,663 B1 | | 4/2002 | Dinkelacker |
| 6,431,867 B1 | * | 8/2002 | Gittelson et al. ............ 433/173 |
| 6,464,500 B1 | | 10/2002 | Popovic |
| 6,527,554 B2 | | 3/2003 | Hurson et al. |
| 6,619,958 B2 | | 9/2003 | Beaty et al. |
| 6,626,911 B1 | | 9/2003 | Engman et al. |
| 6,652,765 B1 | | 11/2003 | Beaty |
| 6,854,972 B1 | | 2/2005 | Elian |
| 6,939,135 B2 | | 9/2005 | Sapian |
| 2001/0021498 A1 | | 9/2001 | Osorio et al. |
| 2002/0182567 A1 | | 12/2002 | Hurson et al. |
| 2003/0031981 A1 | | 2/2003 | Holt |
| 2003/0031982 A1 | | 2/2003 | Abarno |
| 2003/0068599 A1 | | 4/2003 | Balfour et al. |
| 2003/0124489 A1 | | 7/2003 | Hurson et al. |
| 2005/0014108 A1 | | 1/2005 | Wohrle et al. |
| 2005/0214714 A1 | | 9/2005 | Wohrle |

FOREIGN PATENT DOCUMENTS

| | | |
|---|---|---|
| DE | 250 052 A1 | 9/1987 |
| DE | 43 39 060 A1 | 9/1993 |
| EP | 0 705 574 | 4/1996 |
| EP | 0 820 737 | 1/1998 |
| EP | 0 868 889 A1 | 10/1998 |
| EP | 0879580 | 11/1998 |
| EP | 1 013 236 | 12/1998 |
| FR | 2 317 904 | 2/1977 |
| FR | 2634369 | 7/1988 |
| GB | 1291470 | 10/1972 |
| IT | 540713 | 3/1956 |
| JP | 08-117250 | 5/1996 |
| JP | 10-033562 | 2/1998 |
| WO | WO 96/29020 | 9/1996 |
| WO | WO 97/37610 | 10/1997 |
| WO | WO 98/42273 | 10/1998 |
| WO | WO 00/32134 | 6/2000 |
| WO | WO 00/47127 | 8/2000 |
| WO | WO 01/49199 A2 | 7/2001 |
| WO | WO 01/49199 A3 | 7/2001 |
| WO | WO 01/50972 A2 | 7/2001 |
| WO | WO 03/028576 | 4/2003 |
| WO | WO 03/059189 | 7/2003 |
| WO | WO 03/000909 | 11/2003 |

OTHER PUBLICATIONS

Kohal et al., "Custom-made root analogue titanium implants placed into extraction sockets". Clinical Oral Implants Research 1997, vol. 8, pp. 386-392.

Heydecke et al., "Optimal Esthetics in Single Tooth Replacement with the Re-implant System: A Case Report". The International Journal of Prosthodontics 1999, vol. 12, pp. 184-189.

Gieloff et al., "Bio-Design-Implatantate Soforimplantate mit dem Re Implant System", ZWR, 104. Jahrg. 1995, Nr. 4, pp. 252-256 (with translation).

Kohal et al., "Wurzelanaloge Titanimplantate (Bio-Design-Implantate) für die Sofortimplantation-Das Re-implant-System". Implantologie 1996, vol. 2, pp. 99-115 (with translation).

Baier, et al., "Future Directions in Surface Preparation of Dental Implants", Journal of Dental Education, 52:788-791.

Bengazi, et al., 1996, "Recession of the soft tissue margin at oral implants", Clinical Oral Implants Research, 7:303-310.

Branemark, et al., 1985, "Tissue-Integrated Prosthesis: Nature and Significance of the Edentulous State"Quintessence Publishing Co., Inc., chapter 2:77-88.

Brunski, John B., 1988, Biomechanics of Oral Implants: Future Research Directions, Journal of Dental Education, 52:775-787.

Buser, et al., 1991, "Tissue Integration of One-Stage ITI Implants: 3 year Results of a Longitudinal Study With Hollow-Cylinder and Hollow-Screw Implants.", The International Journal of Oral & Maxillofacial Implants, 6:405-412.

Buser, et al., 1996m "Comparison of healed tissues adjacent to submerged and non-submerged unloaded titanium dental implants", Clinical Oral Implants Research, 7:11-19.

Chiche, et al., 1998, "Multidisplinary Implant Dentistry for improved Aesthetics and Function", Pract Periodont. Aesthet. Dent., 10:177-186.

Gieloff et al., 1995, Bio-Design-Implantate Sofortimplantate mit dem Re implant System, p. 252-256 ( with English translation).

Gomez-Roman, et al., 1997, "The Frialit-2 Implant System: Five-Year Clinical Experience in Single-Tooth and Immediately Postextraction Applications", The International Journal of Oral & Maxillofacial Implant, 12:299-309.

Jansen, et al., 1997, "Microbial Leakage and Marginal Fit of the Implant-Abutment Interface", The International Journal of Oral & Maxillofacial Implants, 12:527-540.

Kirsch, et al., 1989., "The IMZ Osteointegrated Implant System", Dental Clinics of North America, 33:733-791.

Kohal et al., 1996., "Wurzelanagoge Titanimplantate (Bio-Design-Implantate) für die Sofortimplatnation-Das Re-Implant®-System", p. 99-115 (with English Translation).

Krau\ser, Jack T., 1989., "Hydorxylapatite-Coated Dental Implants", Dental Clinics of North America, 33:879-903.

Langer, et al., 1993, "The Wide Fixture: A Solution for special Bone Situations and a Rescue for the Compromised Implant. Part 1", the International Journal of Oral & Maxillofacial Implants, 8:400-408.

Meffert, Roland M., DDS, 1988, "The Soft Tissue Interface in Dental Implantology", Journal of Dental Education, 52:810-878.

Niznick, Gerald A., Oct. 1989, "A Multimodal Approach to Implant Prosthodontics", Dental Clinics of North America, 33:869-878.

Olsson, et al., 1995, "MkII-A Modified Self-Tapping Branemark Implant: 3-Year Results of a Controlled Prospective Pilot Study", The International Journal of Oral & Maxillofacial Implant, 10:15-21.

Prestipino, et al., Jan./Feb. 1993, "Esthetic High-Strength Implant Abutments. Part 1", Journal of Esthetic Dentistry, p. 29-35.

W. Eugene Roberts, DDS, Ph.D., 1998, "Bone Tissue Interface", Journal of Dental Education, 52:804-809.

Saadoun, et al., 1998, "Peridontal Implications in Implant Treatment Planning of Aesthtic Results", Pract. Periodont. Asthet. Dent., 10:655-664.

Schnitman, et al., 1988, Implants for Partial Edentulism, Journal of Dental Education, 52:725-736.

Siegele, et al., 1989, "Numerical Investigations of the Influence of Implant Shape on Stress Distribution in the Jaw Bone", the International Journal of Oral & maxillofacial Implants, 4:333-340.

Sullivan, et al., May/Jun. 1993, "Considerations for Successful Single tooth Implant Restorations", Journal of Esthetic Dentistry, 5:119-124.

Wennerberg, et al., "Design and Surface Characteristics of 13 Commercially Available Oral Implant Systems", International Journal of Oral & Maxillofacial Implants, 8:622-633.

F.A. Young, D.Sc., 1988, "Future Directions in Dental Implants Materials Research", Journal of Dental Education 52:770-774.

International Search Report for Application No. PCT/US2003/00909 mailed May 15, 2003, in 3 pages.

Straumann Dental—Brochure; May 2000.

Dinkelacker, Wolfgang, "Vergleighende Untersuchung zur Passform metallkeramischer Kronen auf gegossener und galvanish hergestellter metallener Substruktur" Medizinischen Fakultat (Klinische Medizin) der Eberhard-Karls-Universitat Tubingen, 1990.

Notice of Opposition dated Jan. 19, 2010 for European Patent No. EP1467674, issued Apr. 15, 2009.

* cited by examiner

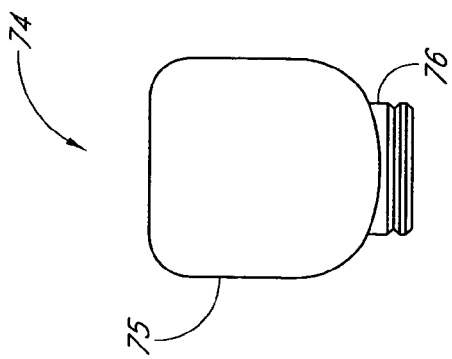
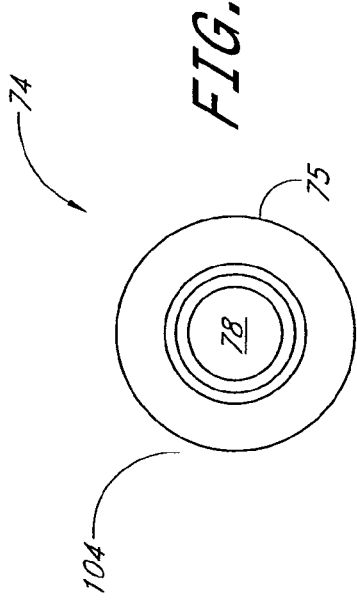
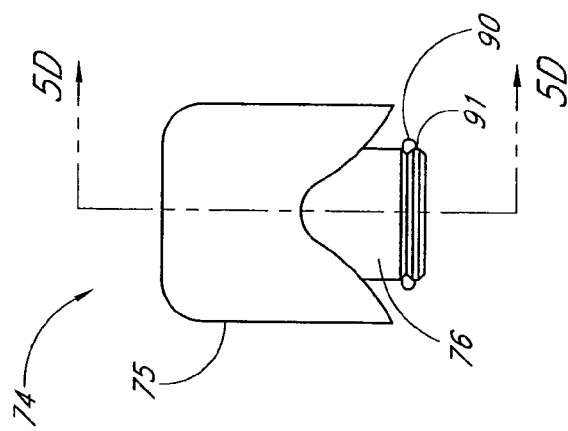
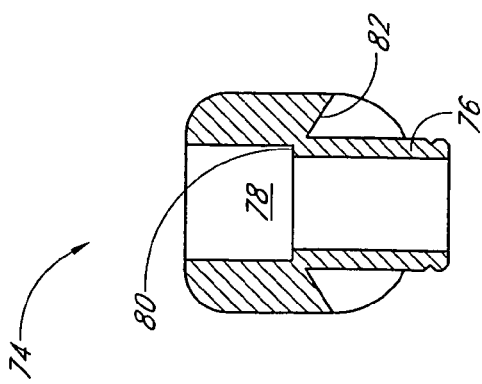
FIG. 5B
FIG. 5C
FIG. 5A
FIG. 5D

DENTAL IMPLANT SYSTEM

PRIORITY INFORMATION

This application is a divisional of U.S. patent application Ser. No. 10/341,531, filed Jan. 13, 2003, now abandoned, which claims the priority benefit under 35 U.S.C. §119(e) of Provisional Application 60/347,723 filed Jan. 11, 2002, the entire contents of these applications are hereby incorporated by reference herein.

BACKGROUND OF THE INVENTION

1. Field of the Invention

The present invention relates generally to dental implants and, more particularly, to an improved dental implant system.

2. Description of the Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone) of a patient. The oral surgeon first accesses the alveolar bone through the patient's gum tissue and removes any remains of the tooth to be replaced. Next, the specific site in the alveolar bone where the implant will be anchored is widened by drilling and/or reaming to accommodate the width of the dental implant to be implanted. Then, the dental implant is inserted into the hole, typically by screwing, although other techniques are known for introducing the implant in the jawbone.

After the implant is initially installed in the bone, a temporary healing cap is secured over the exposed proximal end in order to seal an internal bore of the implant. The patient's gums are then sutured over the implant to allow the implant site to heal and to allow desired osseointegration to occur. Complete osseointegration typically takes anywhere from four to ten months.

During stage II, the surgeon reaccesses the implant fixture by making an incision through the patient's gum tissues. The healing cap is then removed, exposing the proximal end of the implant. Typically, an impression coping is attached to the implant and a mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or attached to the implant during stage I. In such a procedure, stages I and II are effectively combined in to a single stage.

Stage III involves fabricating and placement of a cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosethesis to the final abutment.

The dental implant is typically fabricated from pure titanium or a titanium alloy. The dental implant typically includes a body portion and a collar. The body portion is configured to extend into and osteointegrate with the alveolar bone. The top surface of the collar typically lies flush with the crest of the jawbone bone. The final abutment typically lies on the top surface and extends through the soft tissue, which lies above the alveolar bone. As mentioned above, the abutment supports the final prostheses. Typically, the coronal or crown portion of the collar and the portions of the final abutment that extend through the soft tissue have a machined or polished surfaces. This arrangement is believed in the art to prevent the accumulation of plaque and calculus and facilitates cleaning.

SUMMARY OF THE INVENTION

One aspect of the present invention includes the recognition that the body's natural defense mechanisms tend to provide approximately a 2-3 millimeter zone of soft tissue between the abutment-implant interface (i.e., microgap) and the alveolar crest. This zone is referred to as the "biological width" and is present around natural teeth as well as dental implants. The biological width typically extends 360 degrees around the implant and lies coronal to the alveolar crest and apical to the prosthetic crown margin (approximately 2.5-3 millimeters). The biological width consists of approximately 1 millimeter gingival sulcus, 1 millimeter epithelial attachment and 1 millimeter connective tissue attachment. In prior art implants, the abutment-implant interface typically lies flush with the alveolar crest. As such, the bone tissue is reabsorbed and the alveolar crest retreats until the proper biological width can be reestablished. This bone loss is undesirable both aesthetically and structurally.

Another aspect of the invention is the recognition that the prior art typically provides for a flat interface (i.e., microgap) between the abutment and the collar of the implant. However, due to the irregular configuration of the alveolar crest, a flat interface makes it difficult to conform to a proper biological width in all 360 degrees around the implant. A proper biological width that does not extend for all 360 degrees around the implant can produce undesirable bone loss.

Therefore, one embodiment of the present invention comprises a dental implant assembly for supporting a dental prosthesis. The assembly comprises a dental implant having a body portion located at a distal end of the dental implant. The body portion is configured to lie at least substantially below a crest of a patient's jawbone. A collar portion is located at a proximal end of the dental implant. The collar portion forms a top surface, which defines an outer edge that has at least one peak and valley to match the contours of a patient's soft tissue. A central bore extends through the collar portion and into the implant body portion. The central bore includes a threaded portion and a post portion. The assembly also includes an abutment comprising a post configured to fit within the post portion of implant. A final restoration is configured to fit over the upper portion of the abutment and has an implant mating surface that is configured to mate with the mating surface of the dental implant.

Another embodiment of the present invention comprises a dental implant assembly for supporting a dental prosthesis. The assembly comprises a dental implant having body portion located at a distal end of the dental implant. The body portion is configured to lie at least substantially below a crest of a patient's jawbone. A collar portion is located at a proximal end of the dental implant. The collar portion forms a mating surface which defines an outer edge that has a generally scalloped shape. A central bore extends through the collar portion and into the implant body portion. The central bore includes a threaded portion and a post portion. A healing abutment comprises a post configured to fit within the post portion of the central bore and including an upper portion and implant mating surface that is configured to mate with the mating surface of the dental implant.

Another embodiment of the present invention is dental implant assembly for supporting a dental prosthesis. The assembly comprises a dental implant and an insertion tool. The dental implant comprises a body portion located at a distal end of the dental implant. The body portion is configured to lie at least substantially below a crest of a patient's jawbone. The collar portion is located at a proximal end of the dental implant. The collar portion forming an abutment mating surface which defines an outer edge that has at least one peak and one valley. A central bore extends through the collar portion and into the implant body portion. The central bore includes a threaded portion and a post portion. The insertion tool comprises a post configured to fit within the post portion of the central bore and at least one depth marker for indicating the position of the outer edge. The assembly also comprises complementary mating surfaces between the post of the insertion tool and the post portion of the central tool. The complementary mating surfaces are configured to prevent relative rotation between the dental implant and the insertion tool.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of this invention will now be described with reference to the drawings of a preferred embodiment which is intended to illustrate and not to limit the invention. The drawings contain the following figures:

FIG. 5A is a front view of a healing cap;

FIG. 5B is a top view of the healing cap of FIG. 5A;

FIG. 5C is a side view of the healing cap of FIG. 5A;

FIG. 5D is a cross-sectional view of the healing cap of FIG. 5A taken at line 5D-5D;

DETAILED DESCRIPTION OF THE PREFERRED EMBODIMENT

Figure 1A:
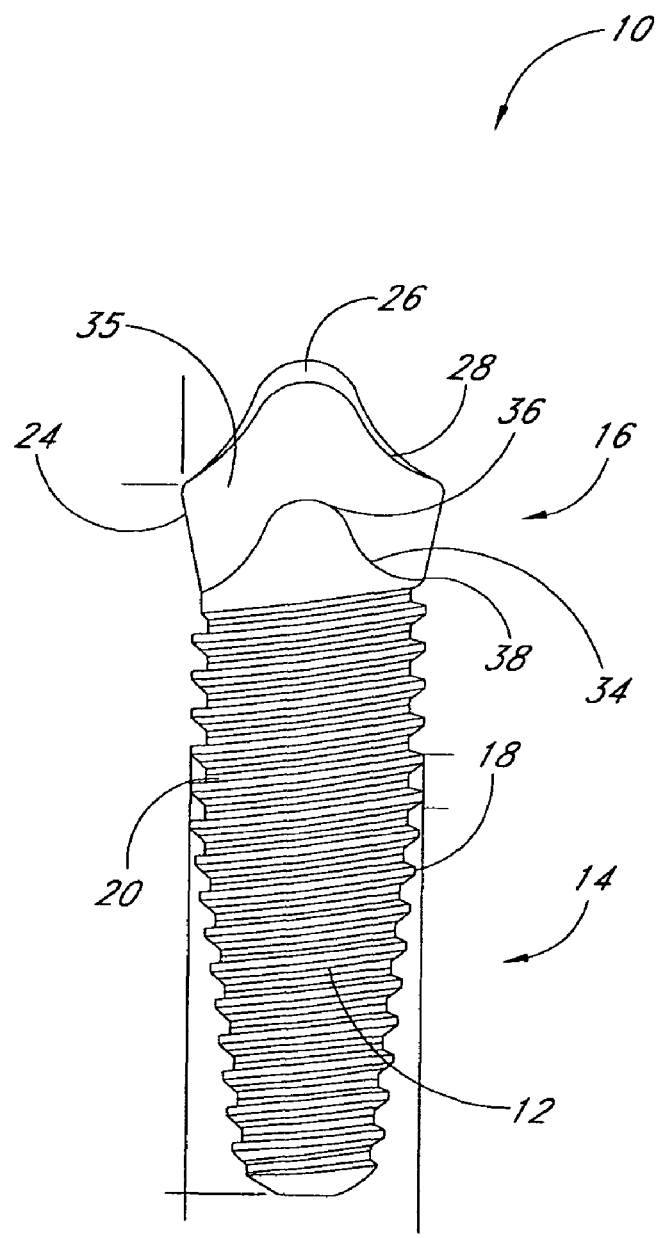
FIG. 1A is a front view of a dental implant.

FIGS. 1A-D illustrate an embodiment of a dental implant 10. In this embodiment, the implant 10 comprises an implant body 12, which preferably includes a lower portion 14 and a collar 16. The lower portion 14 is preferably tapered and includes threads 18 that match preformed threads made along the inner surface of a bore in the patient's jawbone (not shown). However, it should be appreciated that the lower portion 14 can be configured so as to be self-tapping or unthreaded. It should also be appreciated that although the illustrated lower portion 14 is tapered or conical it may also be substantially cylindrical.

As best seen in FIG. 1A, the lower portion 14 preferably has a bone apposition surface 20, which is configured to promote osseointegration. In one embodiment, the bone apposition surface 20 increases the surface area of the lower portion 12. For example, the bone apposition surface 20 can be formed by roughening the lower portion 12 in several different manners, such as, for example, acid-etching, grit blasting, and/or machining. Alternatively, the bone apposition surface 20 can be formed by coating the lower surface with a substance that increases the surface area of the lower portion 12. Calcium phosphate ceramics, such as tricalcium phosphate (TCP) and hydroxyapatite (HA), are particularly suitable materials.

Figure 1C:
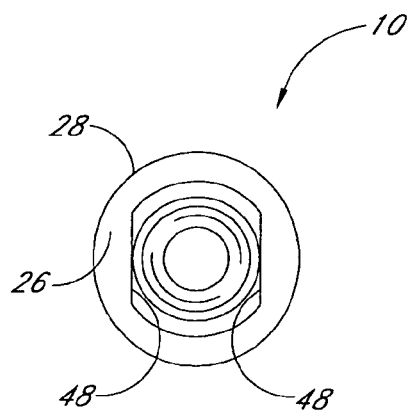
FIG. 1C is a top view of the dental implant of FIG. 1A.
Figure 1D:
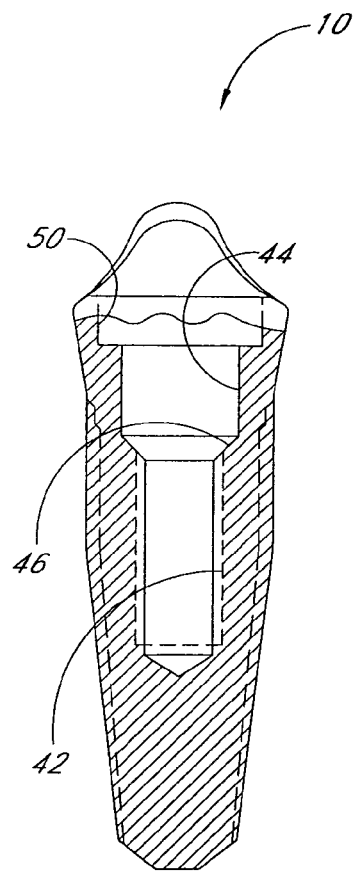
FIG. 1D is a cross-sectional view of the dental implant of FIG. 1A taken along line 1D-1D.
Figure 1B:
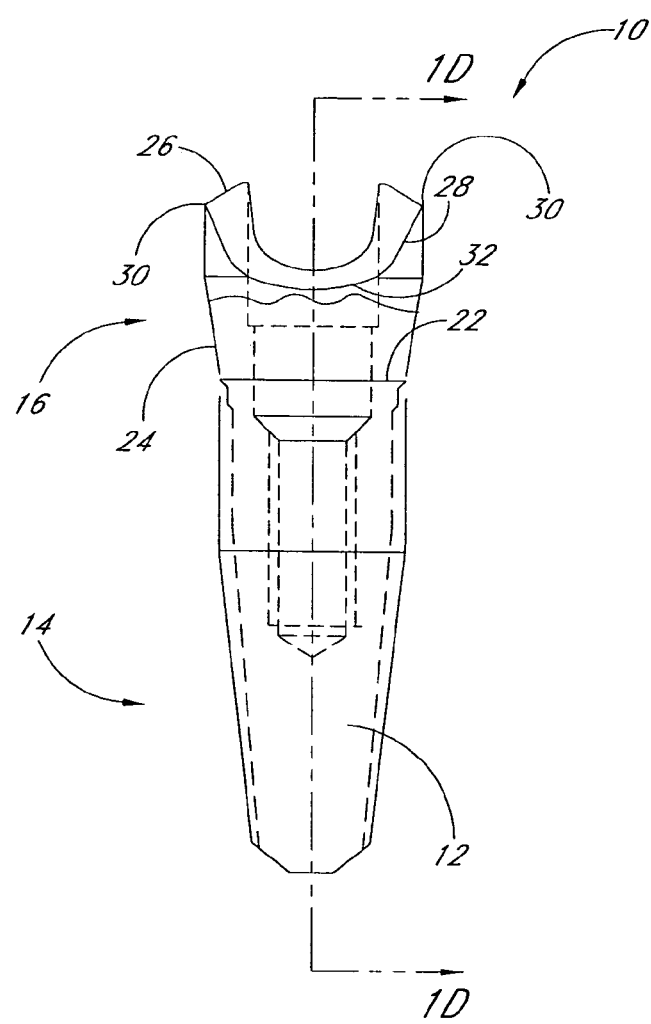
FIG. 1B is a side view of the dental implant of FIG. 1A shown without threads.

The collar 16 preferably lies above (i.e., proximal) the lower portion 12 and in the illustrated embodiment is preferably integrally formed with or permanently affixed to the lower portion 12 at a collar/implant interface 22 (see FIG. 1B). The collar 16 is defined in part by a side wall 24. In the illustrated embodiment, the side wall 24 is tapered with respect to the longitudinal axis of the implant 10 at an angle of approximately 30 degrees. However, in modified embodiments, the side wall 24 can be cylindrical or substantially cylindrical. The illustrated collar 16 also has a substantially circular cross-section (see FIG. 1C). However, in modified embodiments, the collar 16 may have a non-round cross-section.

As best seen in FIGS. 1A-C, the collar 16 includes a top surface 26. As will be described in more detail below, the top surface 26 may support a final restoration. In the illustrated embodiment, an outer edge 28 of the top surface 26 has a curved or scalloped shape with at least one and more preferably two peaks 30 and valleys 32 that follow or at least closely approximate the shape of the naturally occurring contours of a patient's soft-tissue morphology.

In one embodiment, the outer edge 28 is configured so as to be positioned at approximately the same height as the top surfaces of the naturally occurring soft-tissue morphology. In such embodiments, the peaks 30 of the outer edge 28 lie approximately 2-5 millimeters above the collar/body interface 22 while the valleys 32 lie approximately 1-5 millimeters below the peaks 30. In one preferred arrangement, the peak 30 lies approximately 4 millimeters above the collar body interface 25 and the valleys 32 lie approximately 2 millimeters below the peak. Although not illustrated it should be appreciated that in modified embodiments the peaks and valleys may have different heights. That is, the two peaks may have different heights as compared to each other. In a similar manner, the two valleys may have different heights as compared to each other.

As best seen in FIG. 1B, in the illustrated embodiment, the top surface 26 is beveled with respect to a line that is perpendicular to a longitudinal axis of the implant 10. In one preferred embodiment, the top surface 26 may be beveled at an angle of 30 degrees. In modified embodiments, the top surface 26 may be perpendicular to the longitudinal axis (i.e., flat).

With reference to FIG. 1A, a top edge 34 of the bone tissue apposition surface 20 preferably extends above the collar/implant interface 22 and onto the collar 16. As with the outer edge 28, the top edge 34 preferably has a curved or scalloped shape with at least one and more preferably two peaks 36 and valleys 38 that follow or at least closely approximate the shape of the naturally occurring contours of a patient's bone-tissue morphology. In the illustrated embodiment, the peaks 36 and valleys 38 of the top edge 34 are aligned with the peaks 30 and valleys 32 of the outer edge 28.

In the illustrated arrangement, the valleys 38 of the top edge 34 lie slightly above or at the collar/implant interface 22. The peaks 36 may lie approximately 1-5 millimeters above the valleys 38. In one embodiment, the peaks 36 lie approximately 2 millimeters above the valleys 38. As with the outer edge 28, it should be appreciated that in modified embodiments the peaks 36 and valleys 38 may have different heights. That is, the two peaks 36 may have different heights as compared to each other. In a similar manner, the two valleys 38 may have different heights as compared to each other.

The surface 35 of the collar 16 above the top edge may be polished to reduce accumulation of plaque and calculus. In a modified embodiment, the surface 35 may be treated to promote soft-tissue attachment. Such treatments may include roughening and the application of coatings that increase surface area.

With reference to FIG. 1D, the implant 10 preferably includes a central bore 40. In the illustrated embodiment, the central bore 40 includes a threaded section 42 for receiving a threaded portion of a bolt or screw (described below) and post-receiving section 44, which preferably includes a tapered portion 46 adjacent the threaded section 42. The post-receiving 44 section may include anti-rotational features, such as, for example, flat sides, grooves, and or indentations. In the illustrated arrangement, the anti-rotational feature comprises a pair of flat sides 48 (see FIG. 1C), which are positioned in an enlarged diameter portion 50 of the post-receiving section 44.

Figure 2B:
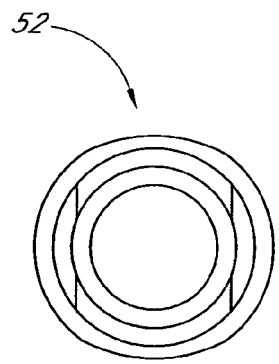
FIG. 2B is a top view of the abutment of FIG. 2A.
Figures 2A, 2D:
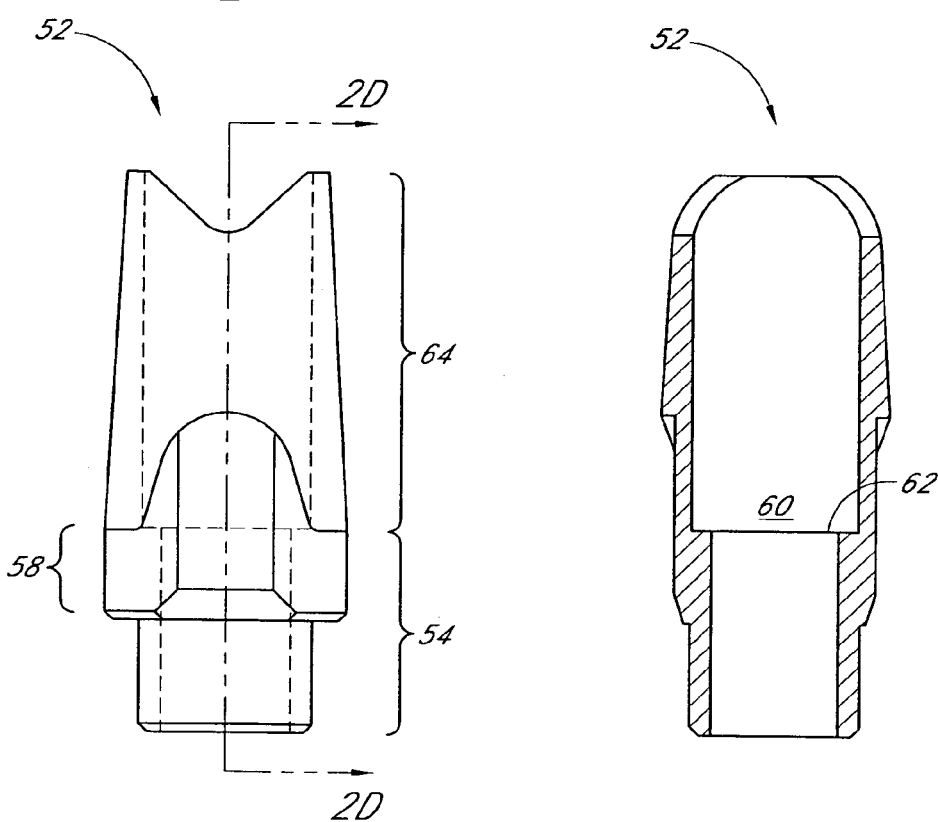
FIG. 2A is a front view of an abutment configured to mate with the implant of FIG. 1A.
FIG. 2D is a cross-sectional view of the abutment of FIG. 2A taken along line 2D-2D.
Figure 2C:
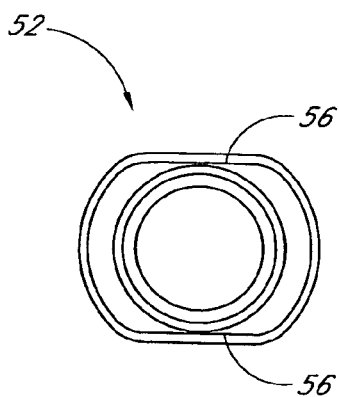
FIG. 2C is a bottom view of the abutment of FIG. 2A.

FIGS. 2A-D illustrate an abutment 52, which is configured to mate with the implant 10 described above. In the illustrated arrangement, the abutment 52 includes a lower portion 54 (see FIG. 2A) that is configured to fit within the post-receiving section 44 of the implant 10. As mentioned above, the post-receiving section 44 may include anti-rotational features. If the post-receiving section 46 includes such anti-rotational features, the lower portion 54 preferably includes corresponding structures so as to prevent the abutment 52 from rotating with respect to the implant body 10. Accordingly, the lower portion 54 of the illustrated embodiment includes a pair of flat sides 56 (FIG. 2C) on an enlarged diameter section 58 of the lower portion 54 (FIG. 2A).

As best seen in FIG. 2D, the abutment 52 preferably includes a central through bore 60, which includes a shoulder 62. The central bore 60 and shoulder 62 are configured to receive a bolt, which is illustrated in FIGS. 3A and 3B.

Figure 3B:
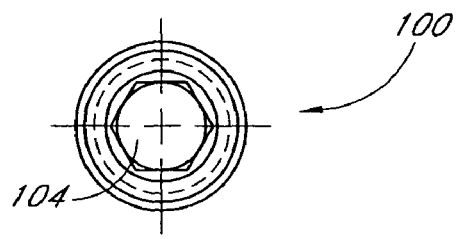
FIG. 3B is a top view of the coupling bolt of FIG. 3A.
Figure 3A:
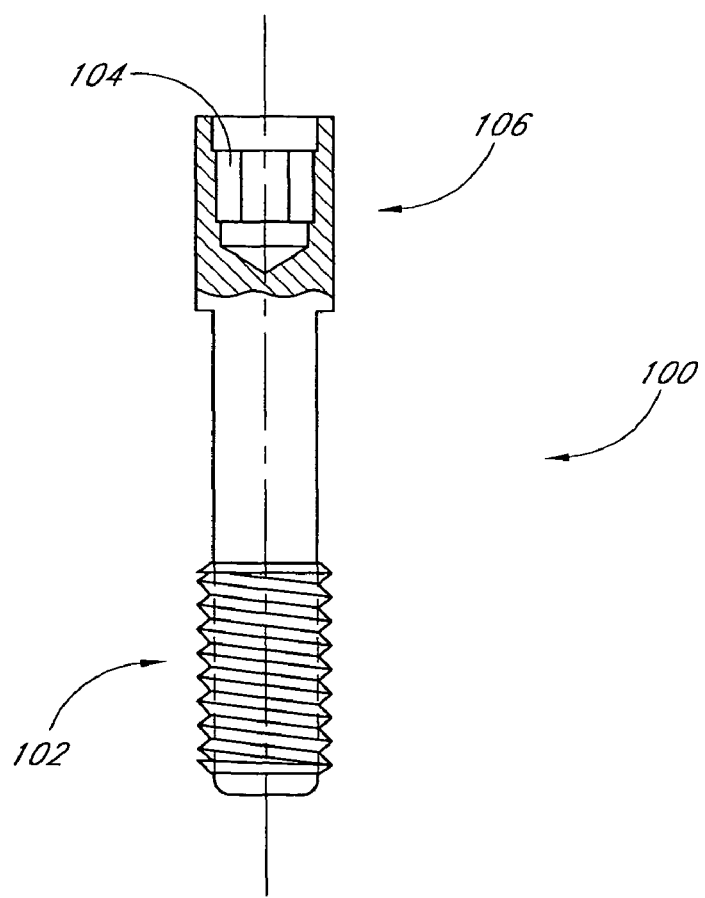
FIG. 3A is a side view of a coupling bolt.

Turning now to FIGS. 3A and 3B, the coupling screw 100 is sized and dimensioned to extend through the bore 60 and to couple the abutment 52 to the implant 10. The coupling screw 100 has an externally threaded lower region 102. The threaded lower region 102 is sized and dimensioned to engage the threads of the threaded chamber 42 of the implant 10. The coupling screw 102 also advantageously includes a hexagonal recess 104 located within a head 106 of the screw 100. The hexagonal recess 104 allows for the insertion of a hexagonally shaped tool such as a conventional Allen® wrench, which can be used to apply rotational force to the coupling screw 100.

With reference back to FIG. 2A, the abutment has an upper portion 64, which, when the lower portion 54 is in the implant 10, is configured to lie above the top surface 26 of the implant 10. The upper portion 64 may be shaped in various ways for supporting various dental components such as, for example, a final restorations and/or other dental components. In the illustrated embodiment, the upper portion 64 has a generally cylindrical shape with a slight taper.

Figure 4A:
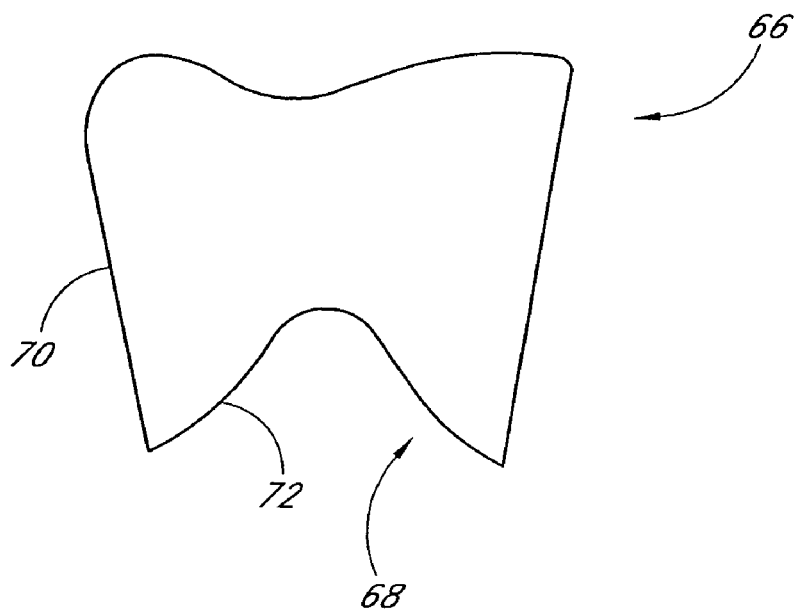
FIG. 4A is a front view of a final restoration configured to mate with the implant of FIG. 1A.
Figure 4B:
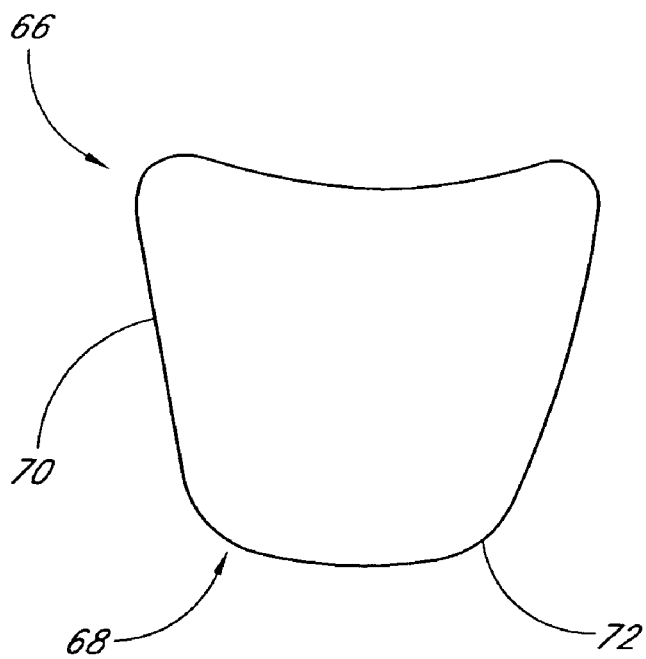
FIG. 4B is a side view of the final restoration of FIG. 4B.

FIGS. 4A-B illustrates a final restoration 66, which can be used with the implant 10 and abutment 52 described above. The final restoration 66 includes an inner surface (not shown), which is configured to fit over the upper portion 64 of the abutment 52. The final restoration 66 preferably also includes a lower surface 68, which is configured to mate with the top surface 26 of the implant 10. Preferably, the lower surface 68 is configured such that when the final restoration 66 is secured on top of the abutment 52, the side wall 24 of the implant and an outer surface 70 of the final restoration 66 form a smooth transition. That is, the dimensions and contours of the outer edge 28 of the top surface 26 preferably closely match the dimensions and contours of an outer edge 72 of the lower surface 68 of the final restoration 66.

The embodiments described above have several advantages. For example, the illustrated implant 10 has a bone apposition surface 20 that follows the naturally occurring contours of the a patient's bone-tissue morphology. This arrangement reduces alveolar bone loss. In a similar manner, the interface between the final restoration 66 and the dental implant 10 follows the naturally occurring contours of the patient's soft-tissue morphology. This arrangement encourages uniform tissue growth above the bone tissue and minimizes the amount of the dental implant 10 that extends above the soft-tissue. In contrast, in prior art implants, substantial portions of the dental implant extend above the soft-tissue, which can create undesirable "shadows" in the gum-tissue. In addition, the interaction between top surface 26 of the implant and the lower surface 68 of the final restoration 66, provides an additional anti-rotational structure between the final restoration 66 and the implant 10.

FIGS. 5A-D illustrate a healing cap 74, which is also configured to mate with the implant 10 described above. The healing cap 74 may be used to cover the dental implant 10 during a healing period, such as, for example, after stage one and/or two surgery.

The healing cap 74 includes a post 76 that is configured to fit within the post receiving section 44 of the dental implant 10. The healing cap 74 preferably includes a central bore 78 with a shoulder 80. The central bore 78 and shoulder 80 are configured to receive a bolt such as the bolt 100 described above. The bolt 100 can extend into the threaded section 42 to secure the healing cap 74 to the dental implant 10.

The healing cap 74 preferably includes a lower surface 82 (see FIG. 5D), which is configured to mate with the top surface 26 of the implant 10. As with the restoration, the top and lower surfaces 26, 82, are preferably configured such that, when the healing cap 80 is secured to the implant 10 a smooth transition is formed between the outer surfaces of the implant 10 and the healing cap 74. An upper surface 75 of the healing cap 74 may have a variety of shapes. For example, in the illustrated embodiment, the upper surface 75 of the healing cap 74 is configured to shape the patient's gums during stage two surgery. In modified embodiments, the upper surface 75 of the healing cap 74 can be configured to facilitate suturing the patient's gums over the implant 10 to allow the implant site to heal and to allow desired osseointegration after, for example, stage one surgery.

In the illustrated embodiment, the post 76 includes a releasable retention feature 90, which is configured to releaseably engage the central bore 40 of the dental implant 10. The post 76 may include a variety of releasable retention features, such as, for example, prongs or compressible material, for creating a releasable retention force between the dental implant 10 and the healing abutment. In the illustrated embodiment, the releasable retention feature 90 comprises a resilient O-ring 90 (shown in cross-section in FIG. 5A) positioned within an annular ridge and recess 91. The O-ring 90 is configured to engage the inner surfaces of the central bore in a friction or interference fit. In this manner, the dental practitioner may temporarily attached the healing cap 74 to the implant 10. The practitioner can then use both hands to manipulate the bolt 100 and a driving instrument to secure the healing cap 74 to the implant 10.

Figure 6A:
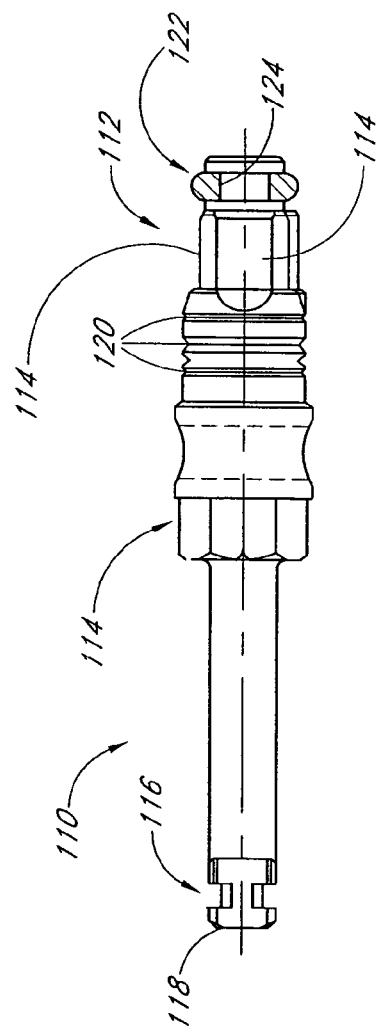
FIG. 6A is a side view of an insertion tool.
Figure 6B:
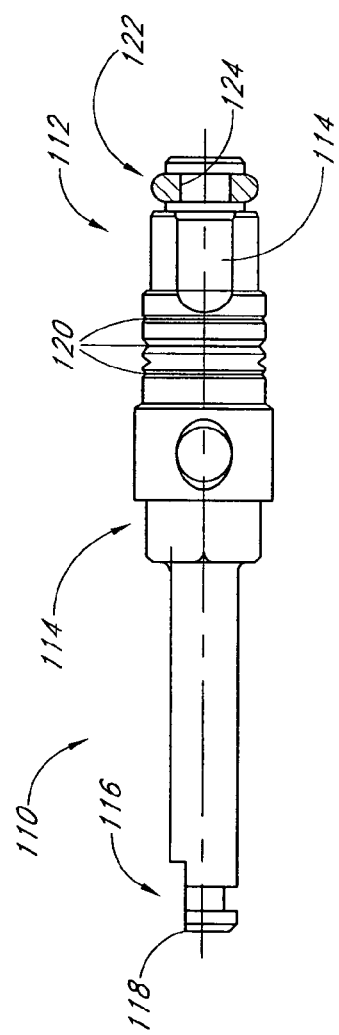
FIG. 6B is a front view of the insertion tool of FIG. 6A.

FIGS. 6A and 6B illustrate an insertion tool 110 that may be used to insert the dental implants described above into a patient's jawbone. The insertion tool 110 includes a post 112 that is configured to fit within the post receiving chamber 44 of the implant. As mentioned above, the post receiving chamber 44 can include anti-rotational features 48. If the post receiving chamber 44 includes such anti-rotational features 48, the post 112 preferably includes corresponding structures so as to prevent the insertion tool 110 from rotating with respect to the implant body 10. In the illustrated embodiment, the post 112 includes two flat sides 114, which corresponds to two flat sides 48 in the post receiving chamber 44 so as to prevent relative rotation between the insertion tool 110 and the dental implant 10.

The insertion tool 110 includes a torque receiving member 114. The torque receiving member 114 is configured to transmit torque from a torque tool (e.g., a wrench) to the insertion tool. In this manner, the torque generated by the tool can be transmitted to the implant 10 through the insertion tool 110. In the illustrated embodiment, the torque receiving member 114 has a hexagonal cross-section. It should be appreciated that the torque receiving member 114 can be formed into a wide variety of other suitable shapes that may be used with efficacy, giving due consideration to the goals of providing anti-rotation between the torque tool and the insertion tool. For example, the torque receiving member 114 may comprise one or more radially inwardly or outwardly extending splines or recesses, flats, polygonal configurations and other anti-rotation complementary surface structures.

The illustrated insertion tool 110 also includes a handpiece receiving portion 116 is sized and dimensioned to fit within a commercial handpiece drill. Typically, the handpiece receiving portion 116 will include a D-shaped key 118 as depicted in FIGS. 6A and 6B. Accordingly, the handpiece receiving portion 116 can be irrotatably locked within the handpiece so that torque can be transmitted from the handpiece to the insertion tool 110. Although a D-shaped key is used in the preferred embodiment, it should be understood that the key may be in the form other shapes as long as that, when in engaged with the handpiece, the key prevents the insertion tool 110 from rotating with respect to the handpiece and from falling out of the handpiece The insertion tool 110 includes a plurality of depth markers 120. In the illustrated embodiment, the depth markers 120 comprise annular grooves. In other embodiments, the depth markers 120 may be formed in a variety of other ways, such as, for example, laser etching, paint, protrusions, etc. The depth markers 120 may be used to guide the dental practitioner when inserting a dental implant into the patient's jawbone. For example, the depth makers 120 are preferably uniformly spaced and arranged so as to indicate the distance from the top of the implant to the top of the gum tissue. In this manner, the thickness of the gum tissue can be determined without requiring incisions to be made around the adjoining/adjacent tissue so as to raise a tissue flap for depth reference. Instead, a probe may be used along the insertion tool 110 to determine the position of the alveolar crest. In such an arrangement, the thickness of the gum tissue may be determined by reference to the depth markers 120 and the implant 10 can be appropriately positioned with respect to the alveolar crest and the top of the gum tissue.

As with the abutment 74, the post 112 of the insertion tool 110 preferably includes a releasable retention feature 122, which is configured to releaseably engage the central bore 40 of the dental implant 10. The post 112 may include a variety of releasable retention features, such as, for example, prongs or compressible material, for creating a releasable retention force between the dental implant 10 and the insertion tool 110. In the illustrated embodiment, the releasable retention feature 122 comprises a resilient O-ring 122 (shown in cross-section in FIGS. 6A and 6B) positioned within an annular ridge and recess 124. The O-ring 122 is configured to engage the inner surfaces of the central bore in a friction or interference fit. In this manner, the dental practitioner may temporarily attached the insertion tool 110 to the implant 10 so as to remove the implant from a package or container.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A dental implant assembly for supporting a dental prosthesis, the assembly comprising:

a dental implant comprising a body portion located at a distal end of the dental implant, the body portion configured to lie at least substantially below a crest of a patient's jawbone, a collar portion located at a proximal end of the dental implant, the collar portion having an outer edge having at least one peak and one valley; a central bore that extends through the collar portion and into the implant body portion, the central bore including a threaded portion and a post portion, an intersection of the surfaces of the collar portion and the central bore defining an inner edge, the inner edge having at least one peak and one valley; a mating surface defined by a surface between the inner edge and the outer edge, wherein the outer edge has a radial dimension greater than the radial dimension of the inner edge, wherein at least a portion of the post portion has a cross-section with a larger radial dimension than the threaded portion, and a healing abutment comprising a post configured to fit within the post portion of the central bore and including an upper portion and implant mating surface that is configured to mate with the mating surface of the dental implant, wherein the implant mating surface comprises an outer edge defining a first width as measured normal to a longitudinal axis of the healing abutment, and wherein the upper portion comprises an outer surface that extends from the outer edge of the implant mating surface to a top surface of the upper portion, and wherein a substantial portion of the outer surface defines a second width as measured normal to the longitudinal axis that is approximately the same as the first width, the outer surface being configured to shape a patient's gums during healing after placement of the implant.

2. The assembly as in claim 1, wherein the abutment includes a retention member for realeasably securing the healing abutment to the implant.

3. The assembly as in claim 2, wherein the retention member comprises an O-ring positioned on the post.

4. The assembly as in claim 1, wherein the dental implant includes a bone apposition surface that extends from the body portion to the collar portion.

5. The assembly as in claim 4, wherein the bone apposition surface has an upper edge positioned on the collar portion, the upper edge having at least one peak and valley to match the contours of a patient's bone tissue.

6. The assembly as in claim 5, wherein a surface of the collar portion between the upper edge and the outer edge is polished.

7. The assembly as in claim 5, wherein the bone apposition surface has an upper edge positioned on the collar portion, the upper edge having at least two peaks and two valleys such that the upper edge matches the contours of a patient's bone tissue.

8. The assembly as in claim 7, wherein a surface of the collar portion between the upper edge and the outer edge is polished.

9. The assembly as in claim 1, wherein the outer edge includes two peaks and valleys to match the contours of a patient's soft tissue.

10. The assembly as in claim 1, wherein the inner edge extends further in the proximal direction than the outer edge, such that the mating surface faces generally away from a longitudinal axis of the dental implant.

* * * * *